United States Patent
Jung et al.

(10) Patent No.: US 6,440,077 B1
(45) Date of Patent: Aug. 27, 2002

(54) APPARATUS AND METHOD FOR THE INTRAVASCULAR ULTRASOUND-GUIDED PLACEMENT OF A VENA CAVA FILTER

(76) Inventors: Matthew T. Jung, 3809 Flowering Grove Ct., Louisville, KY (US) 40241; Hermann W. Kaebnick, 1023 Anchorage Woods Cir., Louisville, KY (US) 40223; Edward V. Kinney, 2600 S. Pope Lick Rd., Louisville, KY (US) 40299; Richard A. Mitchell, 12808 N. Osage Rd., Louisville, KY (US) 40223

( * ) Notice: Subject to any disclaimer, the term of this patent is extended or adjusted under 35 U.S.C. 154(b) by 0 days.

(21) Appl. No.: 09/567,800

(22) Filed: May 9, 2000

Related U.S. Application Data
(60) Provisional application No. 60/137,211, filed on Jun. 2, 1999.

(51) Int. Cl.$^7$ ................................. A61B 8/14
(52) U.S. Cl. ................................. 600/467
(58) Field of Search ................ 600/437, 117, 600/438, 443, 459–470; 604/96, 104, 106; 606/200, 194, 158, 198, 191, 199, 127

(56) References Cited

U.S. PATENT DOCUMENTS

| | | | |
|---|---|---|---|
| 4,793,348 A | | 12/1988 | Palmaz |
| 4,917,097 A | | 4/1990 | Proudian et al. |
| 5,147,379 A | | 9/1992 | Sabbaghian et al. |
| 5,152,777 A | | 10/1992 | Goldberg et al. |
| 5,180,376 A | | 1/1993 | Fischell |
| 5,415,630 A | | 5/1995 | Gory et al. |
| 5,571,086 A | | 11/1996 | Kaplan et al. |
| 5,681,347 A | | 10/1997 | Cathcart et al. |
| 5,722,972 A | | 3/1998 | Power et al. |
| 5,749,848 A | | 5/1998 | Jang et al. |
| 5,769,816 A | * | 6/1998 | Barbut et al. ................. 604/96 |
| 5,836,969 A | | 11/1998 | Kim et al. |
| 5,865,178 A | | 2/1999 | Yock |
| 5,876,344 A | | 3/1999 | Baker et al. |
| 5,893,869 A | | 4/1999 | Barnhart et al. |
| 5,921,931 A | | 7/1999 | O'Donnell et al. |
| 5,931,788 A | * | 8/1999 | Keen et al. ................. 600/462 |
| 5,938,615 A | | 8/1999 | Eberle et al. |
| 6,080,178 A | * | 6/2000 | Meglin ........................ 606/200 |
| 6,267,776 B1 | * | 7/2001 | O'Connell .................. 606/200 |

OTHER PUBLICATIONS

Walsh and Bettmann, Percutaneous Devices for Vena Cava Filtration, Current Therapy in Vascular Surgery, p. 945.

Oppat, Chiou, and Matsumura, Intravascular Ultrasound –Guided Vena Cava Filter Placement, J Endovasc Surg 1999, pp. 285–287, vol. 6.

(List continued on next page.)

*Primary Examiner*—Marvin M. Lateef
*Assistant Examiner*—Ali M. Imam
(74) *Attorney, Agent, or Firm*—Stites & Harbison, PLLC; David W. Nagle, Jr.

(57) ABSTRACT

An apparatus and method for the intravascular placement of a vena cava filter includes an outer sheath, an intravascular ultrasound catheter with an ultrasonic imaging element, a guide wire, and the vena cava filter that is to be deployed. The outer sheath, ultrasound catheter, and guide wire share a common central axis. The ultrasound catheter is enclosed by and is moveable relative to the outer sheath, and the guide wire is enclosed by and is moveable relative to the ultrasound catheter. In the stored position, the filter is secured between the outer sheath and the ultrasound catheter. When the apparatus is introduced into a vein, the ultrasound catheter provides real-time imaging of the vein for identifying the appropriate location for placement of the filter. Once such a location has been identified, the outer sheath is drawn back relative to the ultrasound catheter, exposing the legs of the filter, allowing the legs of the filter to spring free and attach themselves to the wall of the vein.

9 Claims, 5 Drawing Sheets

OTHER PUBLICATIONS

A Method for Inserting Inferior Vena Cava Filters at Bedside in Multitrauma Patients, Vascular Surgery Outlook, 1999, pp. 17–18, vol. 12, No. 5, Thieme Medical Publishers, Inc.

Sing, Smith, Miles and Messick, Preliminary Results of Bedside Inferior Vena Cava Filter Placement, Chest, Jul., 1998, pp. 315–316, vol. 114, No. 1.

Benjamin et al, Duplex ultrasound Insertion of Inferior Vena Cava Filters in Multitrauma Patients, The American Journal of Surgery, Aug. 1999, pp. 92–97, vol. 178.

Oshima, Itchhaporia and Fitzgerald, New Developments in Intravascular Ultrasound, Vascular Medicine, 1998, pp. 281–290, vol. 3.

Rose, Kinney, Valji, and Winchell, Placement of Inferior Vena Caval Filters in the Intensive Care Unit, Journal of Vascular and Interventional Radiology, Jan.–Feb. 1997, pp. 61–64, vol. 8.

Brigade Brachytherapy System Promotional Flier, EndoSonics Corporation, Rancho Cordova, CA, The Netherlands and Germany.

Simon Nitinol Filter Promotional Flier, C.R. Bard, Inc., Covington, Georgia.

Uren, Neal G., An Introduction to Intravascular Ultrasound, 1996, Remedica, Hooper House, Oxford, England.

* cited by examiner

APPARATUS AND METHOD FOR THE INTRAVASCULAR ULTRASOUND-GUIDED PLACEMENT OF A VENA CAVA FILTER

This application claims priority from U.S. provisional application No. 60/137,211 filed Jun. 2, 1999.

BACKGROUND OF THE INVENTION

The present invention relates to an apparatus and method for the intravascular ultrasound-guided placement of vena cava filters, said filters often being necessary in the treatment of deep vein thrombosis.

A deep vein thrombosis is a medical condition wherein a blood clot, or thrombus, has formed inside a vein. Such a clot often develops in the calves, legs, or lower abdomen, but occasionally affects other veins in the body. This clot may partially or completely block blood flow, and, unlike clots in superficial veins, the clot may break off and travel through the bloodstream. Commonly, the clot is caused by a pooling of blood in the vein, often when an individual is bed-ridden for an abnormally long duration of time, for example, when resting following surgery or suffering from a debilitating illness, such as a heart attack or traumatic injury.

Deep vein thrombosis of the lower extremities is a serious problem because of the danger that the clot may break off and travel through the bloodstream to the lungs, causing a pulmonary embolism. This is essentially a blockage of the blood supply to the lungs that causes severe hypoxia and cardiac failure. It frequently results in death.

For many patients, anti-coagulant drug therapies may be sufficient to dissipate the clots. For example, patients may be treated with anticoagulants such as heparin and with thrombolytic agents such as streptokinase. Heparin is available and marketed under such trade names as Heparin Lock™, a product of Abbott Laboratories of Abbott Park, Ill.; and Heparin Sodium™, a product of Pharmacia & Upjohn of Peapack, N.J. Streptokinase is available and marketed under such trade names as Streptase®, a product of Behringwerke Aktiengesellschaft of Frankfurt, Germany; and Kabikinase®, a product of Kabivitrum Aktiebolag of Stockholm, Sweden.

Unfortunately, some patients may not respond to such drug therapy or may not tolerate such therapy. For example, patients may have an acute sensitivity to heparin or may suffer from internal bleeding as a result of such drug therapies. Also, such drug therapies simply may be ineffective in preventing recurrent pulmonary emboli. In such circumstances, surgical procedures are required to prevent pulmonary emboli. Methods for prevention of primary or recurrent pulmonary emboli when anticoagulation therapies are ineffective are well-defined in the prior art. The current standard of therapy for prevention of pulmonary emboli in patients who are classified high-risk or are unable to be anticoagulated is percutaneous insertion and placement of an inferior vena cava filter device. A detailed discussion of the construction and use of such filters is contained in U.S. Pat. No. 5,893,869 issued to Barnhart, which is incorporated herein by reference. Additional information on such filters can also be found in an article entitled "Percutaneous Devices for Vena Cava Filtration" by Daniel E. Walsh and Michael Bettmann contained in *Current Therapy in Vascular Surgery* (3d ed. 1995) at pages 945–949; this article is also incorporated herein by reference.

Placement of these filters is usually accomplished using either the "femoral vein approach" or "jugular vein approach", although alternative approaches, including "axiliary vein approaches", may also be used. There have been a few reports of transabdominal ultrasound being used for placement of filters, but most prior art methods and approaches use fluoroscopy for placement of a guide wire and catheter, as well as for placement and deployment of the filter. Such methods for placement and deployment of a filter also recommend the use of an intravenous dye with contrast angiography.

The fluoroscopy unit may be employed to aid in the placement of the filter in several different ways. For example, the patient is often brought to a operating room or special procedures room, and a fluoroscopy unit is used to identify bony landmarks, allowing the physician to choose the appropriate location for the filter by referencing the bony landmarks. When referencing bony landmarks, placement of the filter is usually done by referencing the lumbar third and fourth vertebrae, making an assumption that the renal veins will be higher than this. However, this method does not provide for an accurate definition of the vena cava size, identification of the position of a clot or thrombus in the vena cava, or accurate identification of the site of the renal veins. It is important to note that, regardless of the method employed in placing the filter, the filter must be placed below the renal veins.

A second and much more accepted method entails the use of a fixed C-arm or fluoroscopic C-arm guidance unit and intravenous contrast in an inferior venacavagram to define the size of the inferior vena cava, to identify the site of the renal veins, and to ascertain the presence or absence of clot at the site proposed for deployment of the filter device. Although this method is often performed in radiology or surgical suites, rather than intensive care units, a general discussion of this method is contained in an article entitled "Placement of Inferior Vena Caval Filters in the Intensive Care Unit" by Drs. Steven C. Rose, Thomas B. Kinney, Karim Valji, and Robert J. Winchell contained in the *Journal of Vascular and Interventional Radiology*, 8:61–64 (1997); this article is also incorporated herein by reference. Deployment of the filter is then performed per the percutaneous filter placement protocols based on the previously performed venacavagram findings. A distinct disadvantage of this method, however, is that the procedure must be performed in either a special x-ray suite or a specially equipped operating room. Thus, significant expense is involved in carrying out this procedure, especially considering that additional staff is often required for a special suite or an operating room. Moreover, the necessity of this specialized location necessitates the transport of an often critically ill or unstable patient from their hospital room to the site of x-ray equipment.

It is therefore a paramount object of the present invention to provide an apparatus and method for intravascular placement of a filter that does not require the use of cumbersome and specialized fluoroscopy equipment and/or an intravenous contrast.

It is a further object of the present invention to provide an apparatus and method for intravascular placement of a filter that can be performed bedside and thus does not necessitate the movement of the patient.

It is still a further object of the present invention to provide an apparatus and method for intravascular placement of a filter that will substantially reduce the overall time and cost of the placement procedure.

These and other objects and advantages of the present invention will become apparent upon a reading of the following description.

SUMMARY OF THE INVENTION

The apparatus of the present invention combines commercially available surgical components into a unitary device for accurate and effective positioning and placement of a vena cava filter. A preferred embodiment of the apparatus of the present invention comprises an outer sheath, an intravascular ultrasound catheter with an ultrasonic imaging element, a guide wire, and the vena cava filter that is to be deployed. The outer sheath, ultrasound catheter and guide wire share a common central axis. The ultrasound catheter is enclosed by and is moveable relative to the outer sheath, and the guide wire is enclosed by and is moveable relative to the ultrasound catheter. In the stored position, the filter is secured between the outer sheath and the ultrasound catheter.

When the apparatus of the present invention is introduced into a vein, the ultrasound catheter provides real-time imaging of the vein for identifying the appropriate location for placement of the filter. Once such a location has been identified, the outer sheath is drawn back relative to the ultrasound catheter, exposing the legs of the filter, allowing the legs of the filter to spring free and attach themselves to the wall of the vein.

Such an apparatus and the use thereof obviates the need for cumbersome and specialized fluoroscopy equipment and/or an intravenous contrast, while also allowing filter placement to be performed bedside, substantially reducing the overall time and cost of the placement procedure.

DESCRIPTION OF THE PREFERRED EMBODIMENTS

The present invention relates to an apparatus and method for the intravascular ultrasound-guided placement of vena cava filters.

Figure 2:
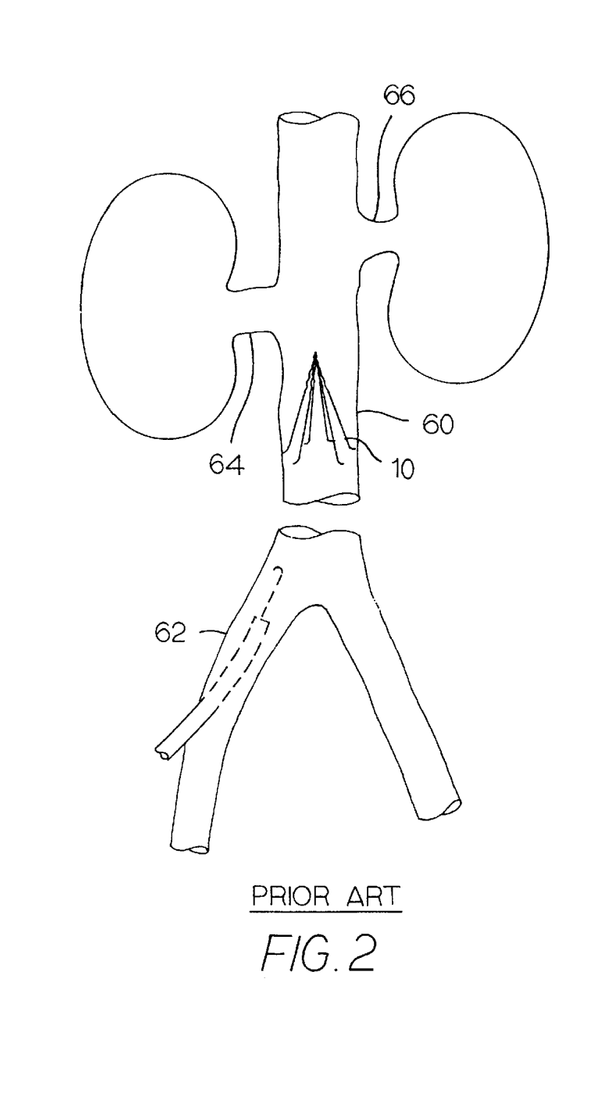
FIG. 2 shows the proper placement of a vena cava filter directly below the renal veins in the inferior vena cava.

Referring first to FIG. 2, this Figure depicts the appropriate placement of a vena cava filter 10 directly below the renal veins 64, 66 in the inferior vena cava 60. Great care must be taken to define the anatomy of this area prior to deployment to avoid encroachment on the renal veins 64, 66 and to ascertain the absence or presence of clots in the vena cava 60. Also, the attending physician must ensure that the vena cava 60 has the appropriate inner diameter for receiving the filter, typically between 10 to 20 mm, and no greater than 28 mm.

Figure 3:
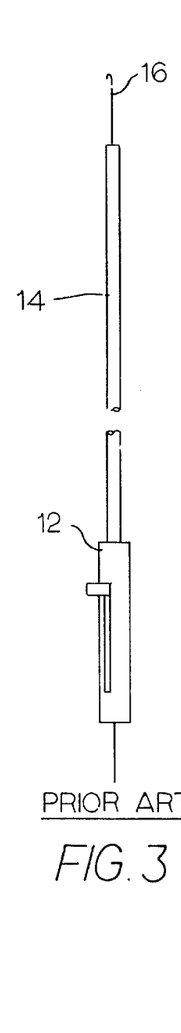
FIG. 3 is a side view of a prior art filter deployment device and associated guide wire wherein the filter is housed within a sheath catheter.
Figure 4:
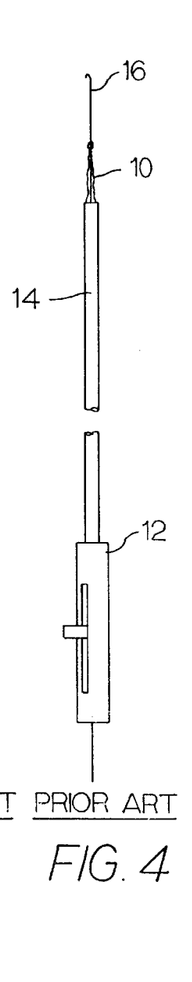
FIG. 4 is side view of the prior art filter deployment device of FIG. 3 wherein the filter is partially deployed.
Figure 5:
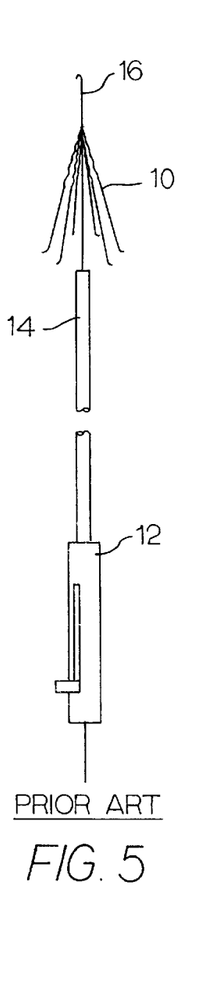
FIG. 5 is side view of the prior art filter deployment device of FIG. 4 wherein the filter is fully deployed.

FIGS. 3–5 show a typical prior art filter 10 and the deployment device 12 for placement of the filter 12. Generally, the deployment device 12 includes a sheath catheter 14 over a guide wire 16. The filter 10 to be deployed is loaded into the distal end of the sheath catheter 14. The catheter 14 is inserted into a vein, and then appropriately positioned using a fluoroscopy unit or other method, as described above. Once so positioned, the outer sheath of the catheter 14 is retracted, allowing the filter 10 to spring open and attach to the walls of the vein. The catheter 14 and guide wire 16 are then withdrawn and removed. Placement of these filters is usually accomplished using fluoroscopy and a contrast angiography. As described above, one common method entails the use of a fixed C-arm or fluoroscopic C-arm guidance unit and intravenous contrast in an inferior venacavagram to define the size of the inferior vena cava, to identify the site of the renal veins, and to ascertain the presence or absence of clot at the site proposed for deployment of the filter 10. Deployment is then performed per the percutaneous filter placement protocols based on the previously performed venacavagram findings.

Figure 6:
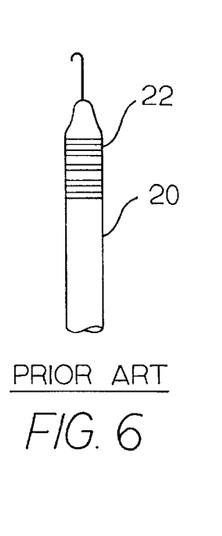
FIG. 6 is a side view of a prior art intravascular ultrasound catheter and associated guide wire.

FIG. 6 of the present application depicts a common prior art intravascular ultrasound catheter (IVUC) 20. Such a catheter is commonly an extruded plastic sheath having a circumferential wall enclosing and protecting the internal wiring and circuitry of the IVUC 20. This particular IVUC includes a solid state imaging element 22. Such IVUCs 20 can provide high quality, real-time imaging of the internal walls of a blood vessel and thus are commonly used in the diagnosis and treatment of fully or partially blocked arteries of the heart, often through the use of an IVUC 20 in conjunction with a percutaneous transluminal coronary angioplasty (commonly referred to as "balloon angioplasty"). For a general discussion of intravascular ultrasound catheters and their use in angioplasty, see U.S. Pat. No. 5,749,848 issued to Jang, et al. and assigned to Cardiovascular Imaging Systems, Inc. of Sunnyvale, Calif. This patent is incorporated herein by reference.

Referring again to FIG. 6, the ultrasonic imaging element 22 that generates the cross-sectional imaging of a blood vessel is housed in the tip of the catheter 20. Signals from the ultrasonic imaging element 22, indicative of reflected ultrasonic waves, are transmitted through internal wires within the catheter 20 to a signal processor.

The design and construction of intravascular ultrasound catheters is well-known in the art. For example, one such IVUC is described in U.S. Pat. No. 4,917,097, issued to Proudian, et al. and assigned to the Endosonics Corporation of Cordova, Calif. This patent is incorporated herein by reference. The present invention does not seek to redesign or improve upon the construction of such catheters, whether they be solid state or mechanical in nature, but rather seeks to employ a intravascular ultrasound catheter in a new and unique apparatus and method for using said apparatus. Indeed, it is contemplated that the apparatus and method of the present invention be carried out by using a commercially available IVUC, such as the EndoSonics® phased array solid state catheter with central wire or the ClearView Ultra™ Intravascular Ultrasound System manufactured and distributed Boston Scientific Corporation of Natick, Mass.

Figure 13:
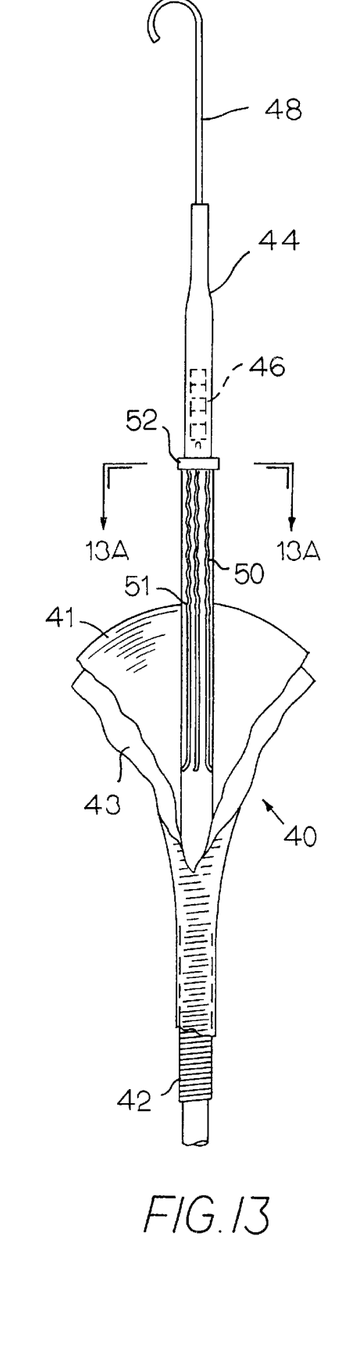
FIG. 13 is a side view of the preferred apparatus of FIGS. 1 and 7–10 with the outer sheath cut away to show the position of the filter within the sheath.
Figures 13A, 14, 15, 15A:
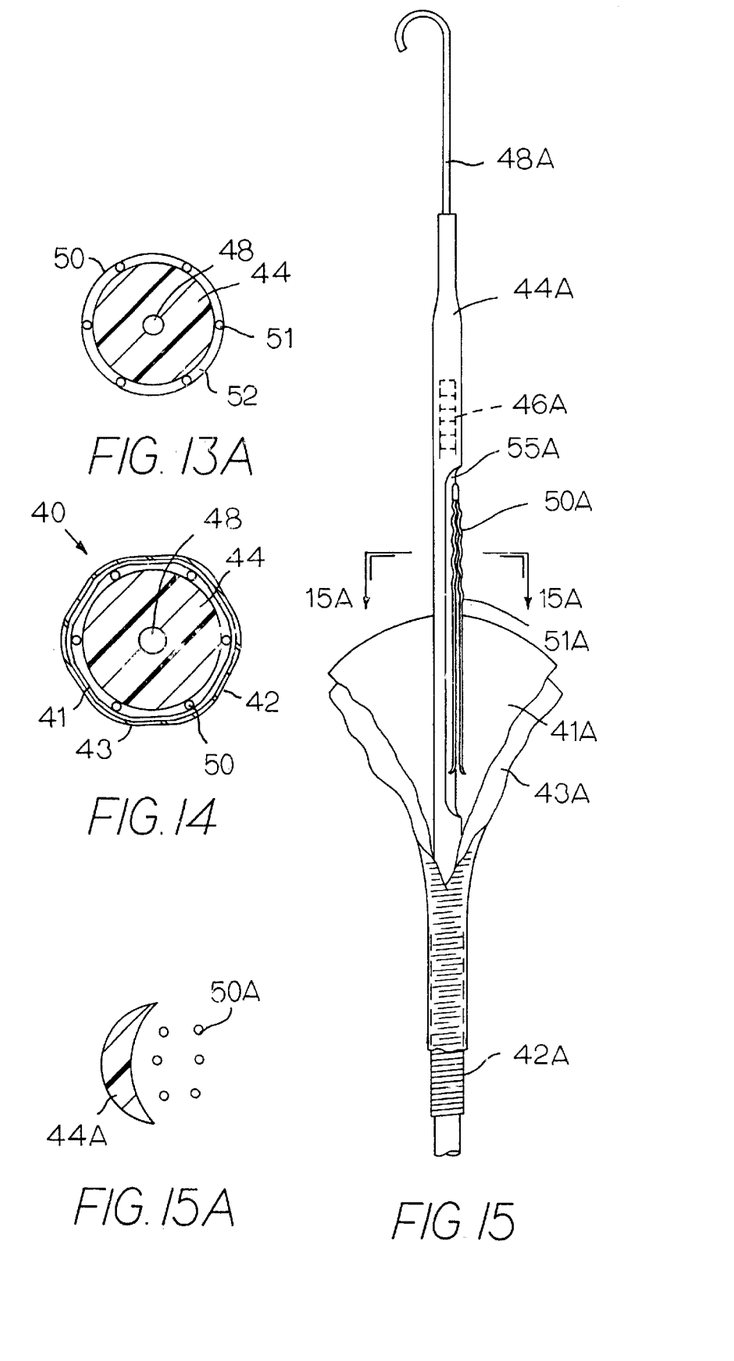
FIG. 13A is a top sectional view of the filter depicted in FIG. 13 taken along lines 13A—13A of FIG. 13.
FIG. 14 is a top sectional view of the preferred apparatus of FIGS. 1 and 7–10 taken along lines 14—14 of FIG. 8.
FIG. 15 is a side view of a second preferred apparatus made in accordance with the present invention.
FIG. 15A is a top sectional view of the filter depicted in FIG. 15 taken along lines 15A—15A of FIG. 15.

FIGS. 13, 13A and 14 depict a first preferred embodiment of the apparatus of the present invention. This apparatus 40 combines commercially available surgical components into a unitary device for accurate positioning and placement of a vena cava filter 50. As shown in FIGS. 13 and 14, this preferred apparatus 40 is comprised of an outer sheath 42, an IVUC 44 with an ultrasonic imaging element 46, a guide wire 48, and the vena cava filter 50 that is to be deployed.

The outer sheath 42 is preferably an 8.0 Fr flexible sheath. The sheath 42 depicted in FIGS. 13 and 14 is part of the Super Arrow-Flex® Percutaneous Introducer Set, Product No. CL-07865, manufactured and distributed by the Arrow International Investment Group of Wilmington, Del. This product is licensed under U.S. Pat. No. 5,180,376 issued to Fischell, which is incorporated herein by reference. As shown, this particular sheath 42 has a wall 41 comprised of a flexible, helical metal coil. The wall 41 is then covered in a thin layer of plastic material 43. Furthermore, the particular sheath 42 has an associated, tapered dilator (not shown) at its distal end for percutaneous insertion of the sheath 42 into the vein. However, the present invention does not require such a dilator as the tapered distal end of the IVUC 44 could serve as an appropriate dilator for percutaneous insertion of the sheath 42 and IVUC 44.

The IVUC 44 preferably has a diameter of approximately 6.0 Fr, allowing it to be easily manipulated and passed through the outer sheath 42. As shown, the IVUC 44 has a solid state imaging element 46, although a mechanical or rotating mirror imaging element could be used without departing from the spirit and scope of the present invention. Again, the present invention does not seek to redesign or improve upon the construction of ultrasonic catheters, whether they be solid state or mechanical in nature, but rather seeks to employ a intravascular ultrasound catheter in a new and unique apparatus and method for using said apparatus.

Finally, the guide wire 48 is preferably a J-tipped or curved wire with a Teflon® coating or similar lubrication. Such coating facilitates smooth movement of the guide wire 48 within a blood vessel, thereby minimizing the hazards of blood clot generation and trauma to internal tissues. In this preferred embodiment, the approximate diameter of this guide wire 48 is 0.035 inches, allowing it to be easily manipulated and passed through the IVUC 44.

The filter 50 itself could be a modified version of a number of commercially available vena cava filters, the only requirement being that the filter 50 have a ring portion 52 at its apex so that it the IVUC 44 may pass through the filter 50. Such a construction of the filter 50 is depicted in FIGS. 13, 13A and 14.

As clearly shown in FIGS. 13 and 14, the outer sheath 42, IVUC 44, and guide wire 48 share a common central axis. Thus, the IVUC 44 is enclosed by and is moveable relative to the outer sheath 42, and the guide wire 48 is enclosed by and is moveable relative to the IVUC 44. In other words, the outer sheath 42 has an annular cross-section and defines an inner diameter. This inner diameter is slightly greater than the outer diameter of the IVUC 44. Similarly, the IVUC 44 has an annular cross-section and defines an inner diameter. This inner diameter is slightly greater than the outer diameter of the guide wire 48. In this regard, as noted above, it is preferred that the distal end of the IVUC 42 be tapered to serve as an appropriate dilator.

The filter 50 slides over the IVUC 44 with the ring portion 52 of the filter 50 resting just below the ultrasonic imaging element 46 of the IVUC 44. In the stored position, the legs 51 of the filter 50 are folded down against the IVUC 44 and are secured between the outer sheath 42 and the IVUC 44. In this regard, although not shown, the IVUC 44 may be provided with a circumferential lip or similar protrusion upon which the filter 50 may rest.

Figure 1:
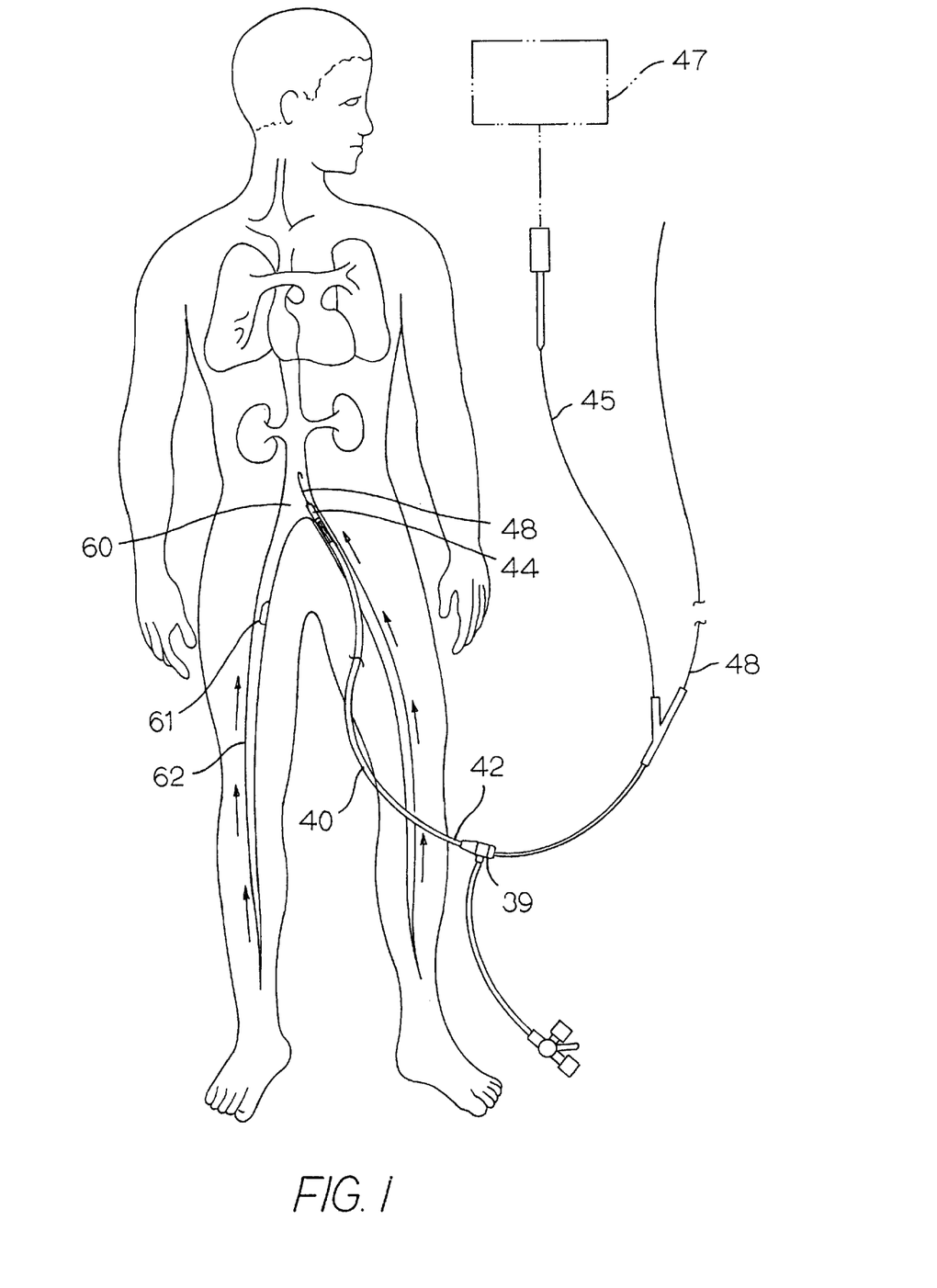
FIG. 1 shows a preferred apparatus made in accordance with the present invention being positioned in a vein for deployment of a vena cava filter.

A better understanding of the construction of the apparatus 40 of the present invention can be achieved through a review of the function and operation of the apparatus 40. Referring first to FIG. 1, a thrombus 61 is present in the right femoral vein 62. As indicated by the arrows, blood flows from the femoral veins 62 through the vena cava 60 toward the heart and lungs, and thus placement of a vena cava filter 50 (not shown) is necessary to prevent the thrombus 61 from traveling to the heart and lungs should it break free.

To deploy the vena cava filter 50 using the preferred apparatus 40, the guide wire 48 is inserted into the vena cava 60, preferably using the Seldinger technique from the femoral position. Over the guide wire 48, the outer sheath 42 and IVUC 44 are passed percutaneously through the femoral vein 62 and into the vena cava 60. In this regard, there is preferably a coupling, as indicated by reference numeral 39 in FIG. 1, that is secured to a distal end of the outer sheath 42. This coupling has an internal seal (not shown) that maintains the positions of the outer sheath 42 and the IVUC 44 relative to one another, thus allowing the outer sheath 42 and the IVUC 44 to be moved together as a unit. When it is necessary to move the IVUC 44 relative to the outer sheath 42, the attending physician must physically maintain the position of the coupling 39 while manually advancing the IVUC 44 through the coupling 39; or, the attending physician may physically maintain the position of the IVUC 44 while drawing back the outer sheath 42 and coupling 39 relative to the IVUC 44.

Figure 11:
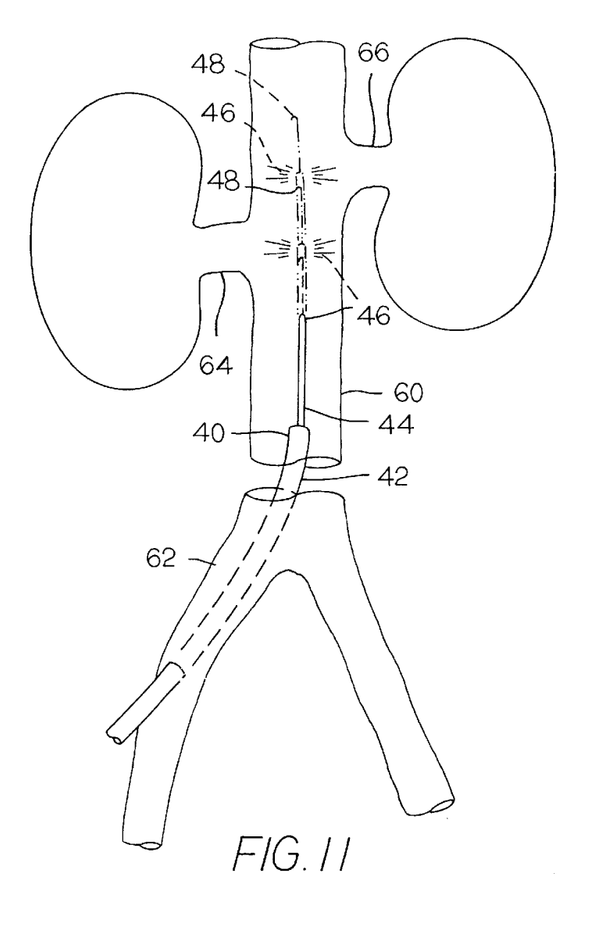
FIG. 11 shows the insertion and positioning of the preferred apparatus of FIGS. 1 and 7–10 to a proper position below the renal veins in the inferior vena cava.
Figure 12:
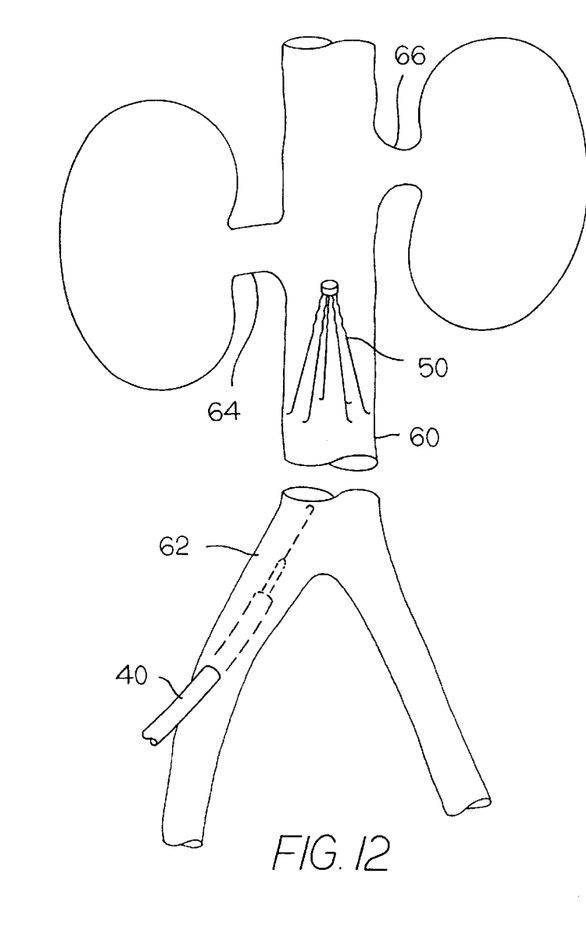
FIG. 12 shows the proper placement of a vena cava filter using the preferred apparatus of FIGS. 1 and 7–10 directly below the renal veins in the inferior vena cava.

As best shown in FIG. 11, as it travels through the femoral vein 62 and into the vena cava 60, the ultrasonic imaging element 46 of the IVUC 44 provides a real-time ultrasonic picture of its passage, thereby assuring proper placement of the filter 50. In this regard, the ultrasonic signals received by the ultrasonic imaging element 46 are transmitted through internal wiring 45 of the IVUC 44 to an external signal processor (as indicated in phantom and by reference numeral 47 in FIG. 1). This real-time imaging of the veins also allows for measurement of the inner diameter of the vena cava 60 and provides a visual confirmation that there is no thrombus in the area selected for deployment of the filter 50. Finally, the ultrasonic imaging allows for extremely accurate identification of the position of the renal veins 64, 66 to further ensure appropriate placement of the filter 50. In this regard, it is preferred that the outer sheath 42 and IVUC 44 are moved through the vena cava 60 past the renal veins 64, 66 (as indicated in phantom in FIG. 11) so that the attending physician can view the portions of the vena cava 60 adjacent the renal veins 64, 66. The outer sheath 42 and IVUC 44 are then drawn back to an appropriate position below the renal veins 62, 64 for deployment of the filter 50. After deployment of the filter 50, the preferred apparatus 40, sans the filter 50, is withdrawn from the vena cava 60, as shown in FIG. 12.

Figure 7:
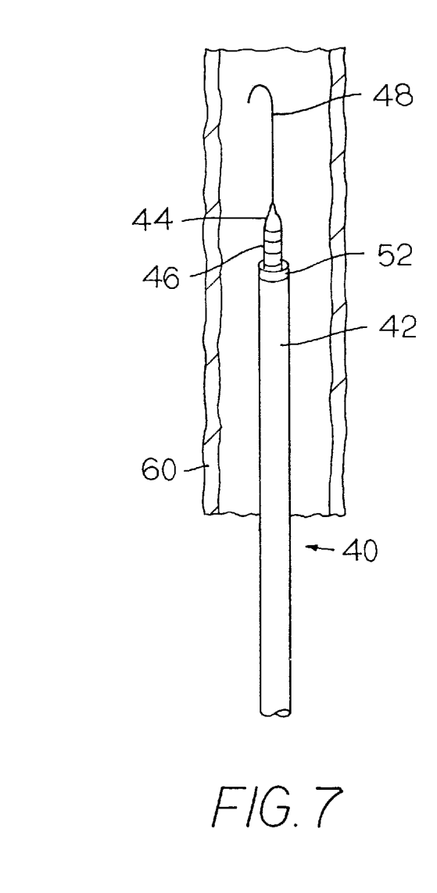
FIG. 7 shows the preferred apparatus of FIG. 1 being positioned in a vein for deployment of a vena cava filter.

FIGS. 7–10 demonstrate, in greater detail, the deployment of the filter 50 using the preferred apparatus 40 described above. As shown in FIG. 7, in its stored position, only the ring portion 52 of the filter 50 extends beyond the distal end of the outer sheath 42. The ultrasonic imaging element 46 of the IVUC 44 extends just beyond the ring portion 52 of the filter 50, or in front of the filter 50. The positioning of the ultrasonic imaging element 46 of the IVUC 44 in front of the filter 50 provides for a clear, unobstructed ultrasonic picture of the femoral vein 62 (as shown in FIG. 11) and vena cava 60 as the preferred apparatus 40 is moved through the veins and into position for deployment of the filter 50. Again, this real-time ultrasonic imaging of the veins also allows for measurement of the inner diameter of the vena cava 60 for appropriate placement of the filter 50, and provides a visual confirmation that there is no thrombus in the area selected for deployment of the filter 50.

Figure 8:
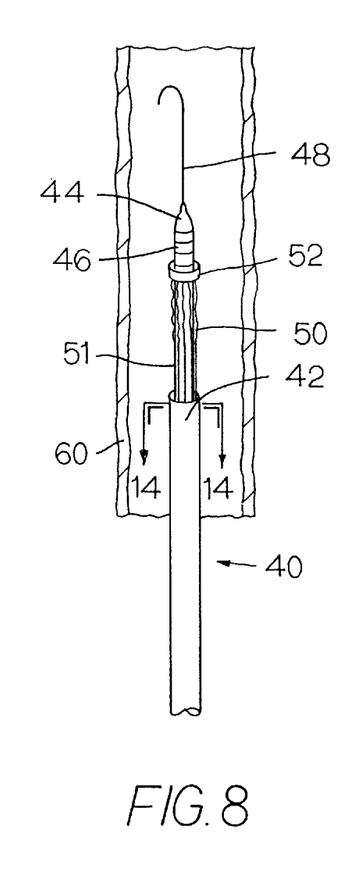
FIG. 8 shows partial deployment of the vena cava filter using the preferred apparatus of FIGS. 1 and 7.
Figure 9:
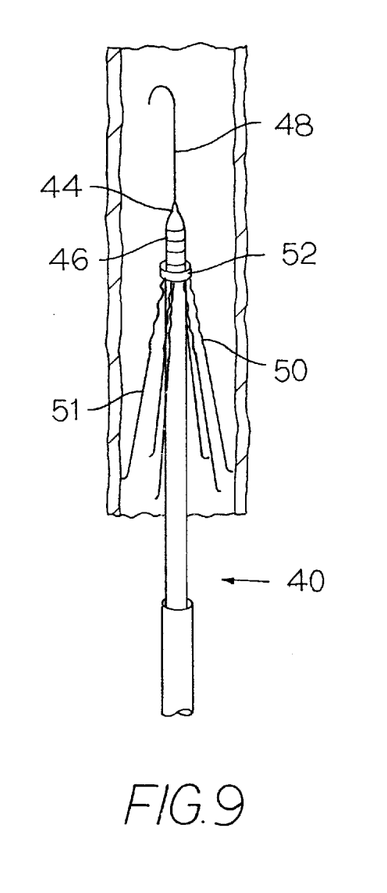
FIG. 9 shows full deployment of the vena cava filter using the preferred apparatus of FIGS. 1 and 7.

Referring now to FIG. 8, once the appropriate location for deployment of the filter 50 has been identified, the outer sheath 42 is drawn back relative to the IVUC 44. In other words, the outer sheath 42 is retracted while the position of the IVUC 44 is maintained. This exposes the legs 51 of the filter 50. Once the outer sheath 42 has been sufficiently retracted, the legs 51 of the filter 50 spring free and attach themselves to the wall of the vena cava 60, as shown in FIG. 9.

Figure 10:
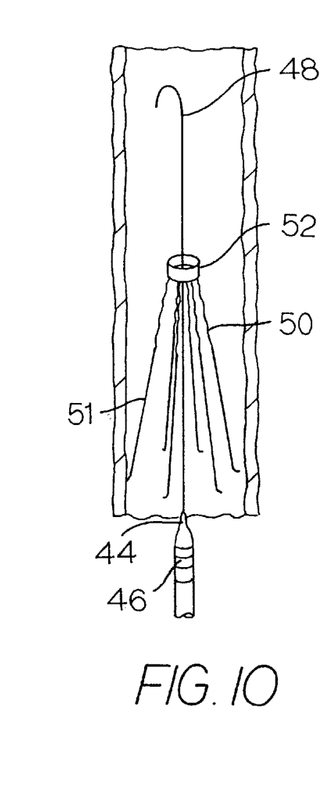
FIG. 10 shows the ultrasonic catheter of the preferred apparatus of FIGS. 1 and 7 being withdrawn through the fully deployed vena cava filter.

With the filter 50 in place in the vena cava 60, the IVUC 44 can be withdrawn through the filter 50, as shown in FIG. 10. As the IVUC 44 is withdrawn, the real-time ultrasonic imaging is used to evaluate the filter 50 to ensure that the struts and hooks of the filter 50 have properly attached to the walls of the vena cava 60.

FIGS. 15 and 15A depict a second preferred embodiment of the present invention, an embodiment which is considered the best mode for carrying out the invention. This preferred apparatus 40A is similarly comprised of an outer sheath 42A, an IVUC 44A with an ultrasonic imaging element 46A, a guide wire 48A, and the vena cava filter 50A that is to be deployed.

Again, the outer sheath 42A is preferably an 8.0 Fr flexible sheath which has a wall 41A comprised of a flexible, helical metal coil encased in a thin layer of plastic material 43A. The IVUC 44A preferably has a diameter of approximately 6.0 Fr, allowing it to be easily manipulated and passed through the outer sheath 42A. Finally, he guide wire 48A is preferably a J-tipped or curved wire with a Teflon® coating or similar lubrication, and having a diameter of approximately 0.035 inches, allowing it to be easily manipulated and passed through the IVUC 44A.

In this preferred embodiment, rather fitting over and around the IVUC 44A, a portion of the side wall of IVUC 44A is removed to provide a channel 55A for accommodating the filter 50 alongside the IVUC 44A. The filter 50A is loaded into this channel 55A and stored in this channel 55A between the outer sheath 42A and the IVUC 44A for deployment. The primary advantage to such a construction is that no modification of existing filter designs in necessary. Virtually any existing filter can be incorporated into this preferred embodiment. For example, a Simon Nitinol Filter®, which is a popular filter available through C.R. Bard, Inc. of Covington, Ga., could be easily incorporated into the apparatus of the present invention. Moreover, existing intravascular ultrasound catheters can be incorporated into this preferred embodiment with only minimal modification of the shaft of the catheter, as described above, and with no change or modification of the functioning components of the IVUC, particularly the ultrasonic imaging element 46A.

Again, deployment of the filter 50A is achieved through proper positioning of the apparatus 40A based on the ultrasonic picture of the vena cava generated by the ultrasonic imaging element 46A of the IVUC 44A, followed by retraction of the outer sheath 42A relative to the IVUC 44A. Such retraction of the outer sheath 42A exposes the legs 51A of the filter 50A, thereby allowing the legs 51A of the filter 50A to spring free and attach themselves to the wall of the vena cava 60. As the filter 50A springs open, it is possible that the IVUC 44 itself may interfere with deployment of the filter 50A. For example, one of the legs 51A of the filter 50A could be caught up in the channel 55A. However, forward and rearward movement of the IVUC 44 relative to the vena cava 60 should free the filter 51A for full deployment. As with the first preferred embodiment described above, with the filter 50A in place in the vena cava, the IVUC 44A can be withdrawn through the filter 50A. And, as the IVUC 44A is withdrawn, the real-time ultrasonic imaging is used to evaluate the filter 50A to ensure that the struts and hooks of the filter 50A have properly attached to the walls of the vena cava.

Each of the above described apparatus could be developed and manufactured using a combination of currently available, FDA-approved intravascular ultrasound catheters, guide wire catheters, introducers and sheaths, and filters. However, it is contemplated that other devices could be developed and used in practicing the present invention without departing from the spirit and scope of the present invention.

As the foregoing description makes clear, there are numerous advantages to the apparatus and methods described above. A primary advantage would be the decreased cost involved in placing filters using ultrasonic imaging rather than fluoroscopy. As mentioned above, fluoroscopy procedures are extremely expensive, often requiring operating room time and specialized staffing. Also, the number of wires and catheters needed for ultrasonic placement as described herein is significantly less than prior art procedures.

Another important advantage is that the apparatus and methods described herein are inherently safer for both patients and staff. Since x-ray equipment is not needed, the patient and staff are not exposed to the dangers of x-ray radiation. Also, an intravenous contrast is not necessary; thus, the patient is not exposed to the risk of anaphylactic shock and death from contrast reaction. Finally, since the procedures described herein can be performed at bedside, critically ill or unstable patients need not be transported. While being transported through poorly or lesser-equipped areas of a hospital, such as an elevator or the radiology suite, emergency situations, such as oxygen desaturations or arrhythmia, are more difficult to deal with because of the lack of experienced personnel and the lack of accessibility to appropriate medications and therapies.

It will be obvious to those skilled in the art that modifications may be made to the preferred embodiments described herein without departing from the spirit and scope of the present invention.

What is claimed is:

1. An apparatus for the intravascular deployment of a filter, comprising:

a flexible outer sheath defining an outer diameter and an inner diameter; and an intravascular ultrasound catheter defining an outer diameter and an inner diameter, and including an ultrasonic imaging element at a distal end thereof, said ultrasound catheter being enclosed along a substantial portion of its length by said flexible outer sheath, and the outer diameter of said ultrasound catheter being less than the inner diameter of said outer sheath, thereby allowing said ultrasound catheter to pass through and move relative to said outer sheath;

wherein, in a stored position, said filter is secured between said outer sheath and said ultrasound catheter near the distal end of said ultrasound catheter;

wherein, when said apparatus is percutaneously introduced into a vein, the ultrasonic imaging element of said ultrasound catheter generates a ultrasonic picture of the vein for identifying an appropriate location for deployment of said filter; and wherein, once said appropriate location is identified, said filter is deployed through movement of said ultrasound catheter relative to said outer sheath.

2. An apparatus for the intravascular deployment of a filter as recited in claim 1, and further comprising a guide wire, said ultrasound catheter defining a central channel for the passage of said guide wire, said guide wire being first introduced percutaneously into said vein, the outer sheath and ultrasound catheter of said apparatus being passed over said guide wire and into said vein for deployment of the filter.

3. An apparatus for the intravascular deployment of a filter as recited in claim 1, wherein said filter includes a central ring portion defining an internal diameter and a plurality of legs secured to and extending from said ring portion; and wherein the internal diameter of said ring portion is greater than the outer diameter of said ultrasound catheter such that, in said stored position, the legs of said filter are secured between said outer sheath and said ultrasound catheter near the distal end of said ultrasound catheter with the legs of said filter folded against and abutting the lateral surface of said ultrasound catheter.

4. An apparatus for the intravascular deployment of a filter as recited in claim 1, wherein said ultrasound catheter defines a channel in a lateral surface thereof for receiving and storing said filter, such that, in said stored position, said filter is secured between said outer sheath and said ultrasound catheter near the distal end of said ultrasound catheter along the lateral surface of said ultrasound catheter.

5. An apparatus for the intravascular deployment of a filter, comprising:

a guide wire for insertion into a blood vessel;

a filter having an active state in which a plurality of filter legs spring open and are adapted to attach to the walls of a surrounding blood vessel;

a flexible outer sheath encasing said filter in a compressed state prior to being in an active state, said sheath being moveable relative to said filter to permit said filter to enter said active state; and a flexible cable moveable relative to said sheath and having an ultrasonic imaging device near the distal end thereof, said filter, sheath, and cable being moveable as a unit when being inserted into said blood vessel.

6. An apparatus for the intravascular deployment of a filter as recited in claim 5, wherein said sheath and cable have annular cross-sections defining respective central openings, said flexible cable positioned within the central opening defined by the annular cross-section of said sheath.

7. An apparatus for the intravascular deployment of a filter as recited in claim 5, wherein said flexible cable has an outer circumferential wall with a portion thereof removed, thereby defining a channel, said filter being positioned in said channel in said compressed state.

8. An apparatus for the intravascular deployment of a filter as recited in claim 6, wherein said guide wire is positioned within the central opening defined by the annular cross-section of said flexible cable and is moveable relative to said cable.

9. A method for the intravascular deployment of a filter using an apparatus including a flexible outer sheath defining an outer diameter and an inner diameter; and an intravascular ultrasound catheter defining an outer diameter and including an ultrasonic imaging element at a distal end thereof, said ultrasound catheter being enclosed along a substantial portion of its length by said flexible outer sheath, and the outer diameter of said ultrasound catheter being less than the inner diameter of said outer sheath, thereby allowing said ultrasound catheter to pass through and move relative to said outer sheath; the steps of said method comprising:

introducing said outer sheath and ultrasound catheter into a vein;

positioning said outer sheath and ultrasound catheter for deployment of said filter;

moving said outer sheath relative to said ultrasound catheter, thereby releasing said filter into said vein; and withdrawing said outer sheath and ultrasound catheter from said vein.

* * * * *